United States Patent [19]

Brittain et al.

[11] Patent Number: 5,430,060
[45] Date of Patent: Jul. 4, 1995

[54] ACETAMIDE DERIVATIVES

[75] Inventors: David R. Brittain, Rochdale; Steven P. Brown; Anthony L. Cooper, both of Bude; Jethro L. Longridge, Macclesfield; Jeffrey J. Morris, Sandbach; John Preston, Knutsford; Linda Slater, Macclesfield, all of England

[73] Assignee: Zeneca Limited, London, England

[21] Appl. No.: 120,760

[22] Filed: Sep. 15, 1993

Related U.S. Application Data

[62] Division of Ser. No. 738,437, Jul. 31, 1991, Pat. No. 5,270,342.

[30] Foreign Application Priority Data

Aug. 2, 1990 [GB] United Kingdom ............... 9016978

[51] Int. Cl.⁶ ............... A61K 31/165; C07C 233/57
[52] U.S. Cl. ............... 514/617; 514/456; 514/520; 514/619; 514/622; 514/866; 549/398; 549/404; 549/407; 558/404; 558/413; 564/166; 564/167; 564/172; 564/174; 564/175; 564/180; 564/181; 564/183
[58] Field of Search ............ 514/617, 623, 866, 619; 564/180, 166, 175, 183

[56] References Cited

U.S. PATENT DOCUMENTS

| | | | |
|---|---|---|---|
| 3,882,247 | 5/1975 | Bullock | 424/327 |
| 4,053,633 | 10/1977 | Goralski | 260/607 |
| 4,309,554 | 1/1982 | Goralski | 549/62 |
| 4,567,004 | 1/1986 | Blank et al. | 260/465 R |
| 4,670,470 | 6/1987 | Firestone | 514/665 |
| 4,831,045 | 5/1989 | Tanouchi | 514/369 |
| 5,153,227 | 10/1992 | Brown et al. | 514/646 |
| 5,270,342 | 12/1993 | Brittain et al. | 514/617 |

FOREIGN PATENT DOCUMENTS

| | | |
|---|---|---|
| 8269 | 2/1980 | European Pat. Off. |
| 252640 | 6/1987 | European Pat. Off. |
| 0304190 | 2/1989 | European Pat. Off. |
| 0340010 | 11/1989 | European Pat. Off. |
| 1229653 | 4/1971 | United Kingdom |
| 2207916 | 2/1989 | United Kingdom |
| 479761 | 5/1976 | U.S.S.R. |
| 9008761 | 8/1990 | WIPO |

OTHER PUBLICATIONS

Brown et al, Chemical Abstracts 112: 7166y Jan. 1, 1990.
STN Printout, 9th Collective Index, Aug. 1978.
J. Chem. Soc., Chemical Communications, 1984, 670.
J. Organic Chemistry, 1978, 43, 3101.
J. Chem. Soc., Chemical Communications, 1978, 362.
J. Organic Chemistry, 1986, 51, 1012–1015.
Chemical Abstracts, vol. 104, Abstract No. 168055, 1986.
J. Prakt. Chem., 1920, 101, 136–137 (Chemical Abstracts vol. 15, 1013–1014).
Rec. Trav. Chim. Pays Bas, 1974, 93, 11–14.
J. Polymer Science, Polymer Chemistry Edition, 1985, 23, 1963–1972.
J. Heterocyclic Chemistry, 1977, 1415–1416.
Tetrahedron, 1969, 25, 181–189.
Chemical Abstracts, 104, Abstract No. 19503d, 1986.
Chemical Abstracts, 103, No. 12, 23 (1985).
Chemical Abstracts 88, No. 19 (1978).
Brown et al., Chemical Abstracts 112, 7166y, Jan. 1, 1990.

*Primary Examiner*—Shailendra Kumar
*Attorney, Agent, or Firm*—Cushman, Darby & Cushman

[57] ABSTRACT

The invention concerns novel N-phenylacetyl and related acyl derivatives of (4-amino-2,6-dimethylphenylsulphonyl)nitromethane and pharmaceutically acceptable salts thereof which are inhibitors of the enzyme aldose reductase and are of value, for example, in the treatment of certain peripheral effects of diabetes and galactosemia. Also disclosed are pharmaceutical compositions containing one of the derivatives and processes for the manufacture and use of the derivatives.

10 Claims, No Drawings

ACETAMIDE DERIVATIVES

This is a division of application Ser. No. 07/738,437, filed Jul. 31, 1991, now U.S. Pat. No. 5,270,342.

This invention concerns novel phenylacetamide derivatives which are inhibitors of the enzyme aldose reductase and which are of value, for example, in the treatment of certain peripheral effects of diabetes or galactosemia. A method of treating one or more of such peripheral effects using an acetamide derivative and pharmaceutical compositions containing such a derivative are also provided. In addition, the invention concerns novel processes for the manufacture of the novel derivatives and for the preparation of medicaments containing any of the said derivatives.

The enzyme aldose reductase is responsible for the catalytic conversion of aldoses, such as glucose and galactose, to the corresponding alditols, such as sorbitol and galactitol respectively, in warm blooded animals such as man. Alditols penetrate cell membranes poorly and, once formed, tend to be removed only by further metabolism. Consequently, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. The enzyme aldose reductase has a relatively low substrate affinity and is generally only effective in the presence of relatively large concentrations of aldose. Such large concentrations are present in the clinical conditions of diabetes (excessive glucose) and galactosemia (excessive galactose). Consequently, aldose reductase inhibitors are useful in the reduction or prevention of the development of those peripheral effects of diabetes or galactosemia which may be due in part to the accumulation of sorbitol or galactitol, respectively, in tissues such as the eye, nerve and kidney. Such peripheral effects include, for example, macular oedema, cataract, retinopathy, neuropathy and impaired neural conduction.

Although a number of aldose reductase inhibitors have been discovered and clinically evaluated, there is a continuing need for alternative inhibitors. In our European patent application, publication number 304,190, there is described a series of (phenylsulfonyl)nitromethane derivatives as inhibitors of the enzyme aldose reductase. We have now discovered that a specific group of novel phenylacetamide derivatives set out below are potent inhibitors of aldose reductase and this is a basis for the present invention.

According to the invention there is provided a novel phenylacetyl derivative of the compound (4-amino-2,6-dimethylphenylsulfonyl)nitromethane having the formula I (set out hereinafter together with the other chemical formulae assigned Roman numerals) wherein $R^0$ and $R^1$ are independently hydrogen, (1–4C)alkyl, (1–4C)alkoxy, cyano or trifluoromethyl, or together constitute (2–6)alkylene, or $R^1$ together with $R^2$ of the adjacent benzene ring A constitutes methylene, ethylene, oxyethylene, ethyleneoxy, methyleneoxymethylene, vinylene, trimethylene or tetramethylene; and on benzene ring A one two or three of the available $R^2$, $R^3$, $R^4$, $R^5$ and $R^6$ are independently selected from hydrogen, halogeno, trifluoromethyl, nitro, cyano, (1–4C)alkyl and (1–4C)alkoxy, and the remainder of $R^2$–$R^6$ is hydrogen; or an adjacent pair of the available $R^2$, $R^3$, $R^4$, $R^5$ and $R^6$ completes (together with the adjoining carbon atoms) a further benzene ring which may itself optionally bear a halogeno, (1–4C)alkyl or (1–4C)alkoxy substituent, another of $R^2$–$R^6$, is hydrogen, halogeno, trifluoromethyl, nitro, cyano, (1–4C)alkyl or (1–4C)alkoxy, and the remainder of $R^2$–$R^6$ is hydrogen; or a pharmaceutically acceptable salt thereof.

It will be appreciated that, depending on the nature of the substituents, (for example, the nature of $R^0$ and $R^1$), the compounds of formula I may contain one or more chiral centres and may exist and be isolated in one or more racemic and enantiomeric forms. It is to be understood that the present invention includes any one of such forms which possesses useful effects as an inhibitor of the enzyme aldose reductase, it being well known in the art how to prepare individual enantiomers (for example, by synthesis from chiral intermediates or by resolution of racemic forms, for example by chromatography on a chiral support) and how to assess their efficacy as aldose reductase inhibitors (for example, by a test procedure described hereinafter).

In this specification it is to be understood that generic terms such as "alkyl" include all isomeric possibilities i.e. both straight and branched chain forms. However, individual radical names such as "propyl" are specific to the form indicated i.e. the straight chain form, any chain branching being specifically indicated as needed.

A particular value for $R^0$ or $R^1$ when it is (1–4C)alkoxy is, for example, methoxy, ethoxy or isopropoxy, of which methoxy is of particular interest.

Particular combinations of $R^0$ and $R^1$ which are of interest include, for example:
(a) $R^0=R^1=$hydrogen; (b) $R^0=$hydrogen and $R^1=$methyl; (c) $R^0=$hydrogen and $R^1=$ethyl; (d) $R^0=$hydrogen or methyl, and $R^1=$cyano; (e) $R^0=$hydrogen or trifluoromethyl and $R^1=$methoxy or ethoxy; and (f) $R^0$ and $R^1$ together=ethylene.

A particular value for $R^0$ and $R^1$ when together they constitute (2–6C)alkylene is, for example, ethylene, 1,1-dimethylethylene, trimethylene, tetramethylene or pentamethylene.

Particular values for generic substituents as defined above on benzene ring A include, for example:
for halogeno: fluoro, chloro and bromo;
for (1–4C)alkyl: methyl, ethyl, propyl, isopropyl and isobutyl; and
for (1–4C)alkoxy: methoxy and ethoxy.

A particular value for an optional substituent which may be present on a second benzene ring when a pair of $R^2$–$R^6$ as defined above complete such a ring is, for example, fluoro, chloro, methyl or methoxy.

A specific group of compounds within the invention comprises bi- or tri-cyclic amides of the formula Ia set out hereinafter wherein Q is methylene, ethylene, oxyethylene, ethyleneoxy, vinylene or trimethylene and the substituents $R^3$–$R^6$ on benzene ring A have any of the meanings defined above, and the pharmaceutically acceptable salts thereof.

A preferred group of compounds of the invention comprises compounds of the formula II set out hereinafter wherein Ra and Rb are independently hydrogen, methyl, ethyl or cyano, or one of Ra and Rb is hydrogen or trifluoromethyl and the other is methoxy, ethoxy or isopropoxy; and benzene ring B is selected from phenyl, 2-halogenophenyl (especially 2-fluoro or 2-chlorophenyl), 2-(1–4C)alkylphenyl (especially 2-methylphenyl), 2-(1–4C)alkoxyphenyl (especially 2- methoxyphenyl), 4-(1–4C)alkoxyphenyl (especially 4-methoxy or 4-ethoxyphenyl) and 2,4,6-tri[(1–4C)alkyl]-phenyl (especially 2,4,6-trimethylphenyl); and the pharmaceutically acceptable salts thereof.

A further group of compounds of particular interest comprises compounds of the formula IIa set out hereinafter wherein Acyl is selected from:
phenylacetyl, (2,4,6-trimethylphenyl)acetyl, (2-methylphenyl)acetyl, (2-fluorophenyl)acetyl, (2-chlorophenyl)acetyl, (2-methoxyphenyl)acetyl, 1-(4-chlorophenyl)-1-cyclopropanecarbonyl, 1-(phenyl)-1-cyclopropanecarbonyl, (4-ethoxyphenyl)acetyl, (R,S)-2-(phenyl)propionyl, (4-methoxyphenyl)acetyl, (R,S)-benzocyclobutanecarbonyl, (2-bromophenyl)acetyl, (2-nitrophenyl)acetyl, 2-(4-chlorophenyl)-2-methylpropionyl, (4-methoxy-3-methylphenyl)acetyl, (3-fluorophenyl)acetyl, (R,S)-2-methoxy-2-(2-fluorophenyl)acetyl, (2-trifluoromethylphenyl)acetyl, (3,4-difluorophenyl)acetyl, (2,6-dichlorophenyl)acetyl, (4-trifluoromethylphenyl)acetyl, (4-chlorophenyl)acetyl, (3-methylphenyl)acetyl, (3-methoxyphenyl)acetyl, 1-phenylcyclopentanecarbonyl, 1-(4-methoxyphenyl)cyclopropanecarbonyl, (2-naphthyl)acetyl, (R,S)-1-(4-chlorophenyl)cyclobutanecarbonyl, (1-naphthyl)acetyl, (2-methyl-6-nitrophenyl)acetyl, (4-fluorophenyl)acetyl, (3,4-dichlorophenyl)acetyl, (2,4-dichlorophenyl)acetyl, (R,S)-2-(4-isobutylphenyl)propionyl, (R)-3,3,3-trifluoro-2-methoxy-2-phenylpropionyl, (S)-3,3,3-trifluoro-2-methoxy-2-phenylpropionyl, (R,S)-2-methoxy-2-(2-methylphenyl)acetyl, (S)-2-methoxy-2-phenylacetyl, (R,S)-1,2,3,4-tetrahydro-1-naphthoyl, (R)-2-methoxy-2-phenylacetyl, (R,S)-2-methoxy-2-phenylacetyl, (R,S)-2-(2-chlorophenyl)-2-methoxyacetyl, (R,S)-2-(2-chlorophenyl)-2-isopropoxyacetyl, 3-indenylcarbonyl, (R,S)-1-indanylcarbonyl, (R,S)-2-(3-fluoro-2-methylphenyl)-2-methoxyacetyl, (R,S)-2-(2,6-difluorophenyl)-2-methoxyacetyl, (2,6-difluorophenyl)acetyl, (1-isochromanyl)carbonyl, (R,S)-2-cyano-2-(phenyl)propionyl, (R,S)-2-methoxy-2-(2-methoxyphenyl)acetyl, (R,S)-2-(2,3-difluorophenyl)-2-methoxyacetyl, (S)-2-phenylpropionyl, (R)-2-phenylpropionyl, (R,S)-2-(2-methylphenyl)-propionyl, (R,S)-2-phenylbutyryl, (R,S)-2-ethoxy-2-(phenyl)acetyl and (R,S)-2-ethoxy-2-(2-methylphenyl)acetyl; and the pharmaceutically acceptable salts thereof.

A still further group of compounds of the invention comprises compounds of the formula IIa wherein Acyl is selected from: (R)-2-methoxy-2-(2-methylphenyl)acetyl, (R,S)-2-ethoxy-2-(2-fluorophenyl)acetyl, 2-(2,3-dimethylphenyl)acetyl, 2-(2,6-dimethylphenyl)acetyl, (R,S)-2-(2,6-difluorophenylpropionyl, (S)-2-methoxy-2-(2-methylphenyl)acetyl, 2-(4-methylphenyl)acetyl, 2-(2-fluorophenyl)propionyl, 2-(2,4-dimethylphenyl)acetyl, (R)-1,2,3,4-tetrahydro-1-naphthoyl, (S)-1,2,3,4-tetrahydro-1-naphthoyl, (R)-2-methoxy-2-(2-methoxyphenyl)acetyl and (S)-2-methoxy-2-(2-methoxyphenyl)acetyl; and the pharmaceutically acceptable salts thereof.

Specific compounds of the invention are set out in the accompanying Examples and are provided together with their pharmaceutically acceptable salts as a further feature of the invention. A group of exemplified compounds which is of particular interest comprises the compounds described in Examples 1–12, 19, 37–44, 47–48, 50–52, 60–68 and 71–74; or a pharmaceutically acceptable salt thereof. Of these, the compounds described in Examples 2, 3, 37–40, 52, 58, 60, 62, 71 and 73, or a pharmaceutically acceptable salt thereof, are particularly preferred.

Suitable pharmaceutically acceptable salts include, for example, alkali metal (such as potassium or sodium), alkaline earth metal (such as calcium or magnesium), ammonium and aluminium salts, and salts with organic bases affording physiologically acceptable cations, such as salts with methylamine, dimethylamine, trimethylamine, piperidine and morpholine.

The novel compounds of the invention may be obtained by standard procedures of organic chemistry already known for the production of structurally analogous compounds, for example as described in our aforementioned European patent application. Such procedures are provided as a further feature of the invention and are illustrated by the following procedures in which $R^1$, $R^0$, benzene ring A and the optional substituents thereon have any of the meanings defined hereinbefore.

(a) (4-Amino-2,6-dimethylphenylsulfonyl)nitromethane is acylated by reaction with a carboxylic acid of the formula III, or with a reactive acylating agent derived therefrom, such as an acid halide, azide, anhydride or mixed anhydride thereof.

When a free acid of formula III is used, the process is preferably carried out in the presence of a suitable condensing agent, for example, a carbodiimide such as 1,3-dicyclohexylcarbodiimide, 1,3-diisopropylcarbodiimide or 1-ethyl-3-(3-dimethylaminopropyl)carbodiimide optionally together with an N-hydroxytriazole such as 1-hydroxybenzotriazole and in a suitable solvent or diluent, for example, methylene chloride or dimethylformamide, and at a temperature in the range, for example, −20° to 35° C. and, preferably, at or near ambient temperature. When 1-ethyl-3-(3-dimethylaminopropyl)-carbodiimide is used as condensing agent, it is conveniently used in the form of a hydrohalide (such as the hydrochloride) salt and, preferably, in the presence of a suitable organic base, for example, triethylamine.

The acid of formula III may also conveniently be utilised in the form of its alkali metal salt, for example, its lithium, sodium or potassium salt. In these cases a suitable condensing agent such as a carbodiimide optionally together with an N-hydroxytriazole is used as described above. However, in this case, when a 1-ethyl-3-(3-dimethylaminopropyl)carbodiimide hydrohalide is used as the condensing agent, no added organic base is required.

A particularly suitable reactive derivative of an acid of formula III is, for example, the acid halide of the said acid, for example the acid chloride or bromide (obtainable, for example, by reaction of the corresponding acid with an agent such as thionyl chloride or bromide), a mixed anhydride of the said acid with a (1–4C)alkanoic acid (such as formic acid) or a hemi(1–4C)alkyl carbonate [obtainable, for example, by reaction of the said acid with, respectively, an appropriate alkanoyl halide or a(1–4C)alkyl chloroformate (such as isobutyl chloroformate), or an azide of the said acid, (obtainable, for example, by reaction of the said acid with diphenylphosphoryl azide and triethylamine or from the corresponding hydrazide of the said acid by reaction with an alkyl nitrite such as t-butyl or amyl nitrite in the presence of strong acid). When a reactive derivative of an acid of the formula III is used in process (a), a suitable base such as a metal carbonate, for example, potassium, sodium, lithium, calcium, barium or magnesium carbonate which calcium carbonate is particularly preferred) or an organic base such as triethylamine, N-methylmorpholine, N-methylpiperidine or 4-(dimethylamino)pyridine is conveniently also present and the reaction is carried out in a suitable solvent or diluent such as dioxan, N,N-dimethylformamide or methylene chloride and a temperature in the range, for example, 0° to 40° C. and, conveniently, at or near ambient temperature. When a compound of formula I in optically form is required, the acid of formula III or the reactive derivative thereof may conveniently be used as a single enantiomeric form.

The starting amino compound, (4-amino-2,6-dimethylphenylsulfonyl)nitromethane, may be made by any of the general methods described in our aforesaid European patent application or as illustrated in the accompanying Examples. The starting carboxylic acids of formula III are in general well known and, in many cases, are commercially available. Alternatively, they may be obtained by procedures already established for structurally analogous carboxylic acids, for example, as is indicated in the accompanying Examples.

(b) A thioether of the formula (IV) is oxidised.

Suitable oxidising agents for this reaction include any of those which are well known in the art for the conversion of thio to sulfonyl groups and which are compatible with the presence of the acylamino and methyl groups which are also present as substituents on the benzene moiety. Thus, for example, hydrogen peroxide, an organic peracid (such as perbenzoic acid) or lead tetraacetate may be used. Alternatively, an alkali metal periodate (such as sodium metaperiodate), persulfate (such as potassium monopersulfate) or permanganate (such as potassium permanganate), or gaseous oxygen in the presence of a suitable catalyst such as platinum, may be employed. The oxidation is preferably carried out in a suitable conventional solvent or diluent for such oxidations, for example in acetic or propionic acid, and at a temperature in the general range, for example 0° to 80° C.

In certain cases, the corresponding sulfoxide derivative of the thioether of formula IV may be formed as an isolable intermediate. The process of the invention also includes the oxidation of such a sulfoxide intermediate to a sulfone of formula I, for example, by reaction with an alkali metal permanganate (such as potassium permanganate) in a suitable solvent such as acetic acid and at a temperature in the range, 20° to 80° C.

The starting thioethers of formula IV may be obtained by conventional procedures of organic chemistry, for example, from a potassium or sodium salt of the corresponding thiophenol of the formula V by conversion to the corresponding thioacetic acid of the formula VI (or a (1-4C)alkyl ester thereof, such as a methyl or ethyl ester) by reaction with chloro- or bromo-acetic acid (or a (1-4C)alkyl ester thereof) in the presence of a suitable base. The acid VI (or a (1-4C)alkyl ester thereof) is then reacted with a (1-5C)alkyl nitrate and an alkali metal (1-6C)alkane, for example propyl nitrate and butyllithium, to give the alkali metal salt of the corresponding 2-nitroacetic acid of the formula VII (or of the (1-4C)alkyl ester thereof). The acids of formula VII are unstable and readily decarboxylate and acidification of the alkali metal salt of an acid of formula VII allows the isolation of a thioether of formula IV. An ester of an acid of formula VII may be hydrolysed, for example, using aqueous base, to the acid of formula VII and then acidified to produce a thioether of formula IV.

The thiophenols of formula V may conveniently be obtained by N-acylation of 4-amino-2,6-dimethylbenzene thiol using a procedure analogous to that in (a) above. 4-Amino-2,6-dimethylbenzene thiol may itself be obtained, for example by reaction of 3,5-dimethylaniline with thiocyanogen (generated in situ from lead(II) thiocyanate and bromine in methyl acetate) or with copper-(II) thiocyanate to give 4-amino-2,6-dimethylphenyl isothiocyanate, which latter is then reduced, for example, with sodium borohydride in ethanol to give the required thiol.

(c) Reacting an alkali metal salt of a 4-N-acylamino-2,6-dimethylbenzenesulfinic acid of the formula VIII with nitromethane and iodine in the presence of an alkali metal (1-6C)alkoxide such as potassium t-butoxide or sodium methoxide.

The reaction is preferably carried out in the presence of a suitable polar solvent, for example, 1,3-dimethyl-3,4,5,6-tetrahydro2(1H)-pyrimidinone (DMPU) or N,N-dimethylformamide (which are preferred), or N-methyl-2-pyrrolidone, and at a temperature in the range, for example, −30° to 20° C. and, conveniently, at about 0° C. The nitromethane is generally present in an excess.

The starting alkali metal salt may be obtained, for example, from the corresponding sulfinic acid of formula VIII by reaction with the appropriate alkali metal hydroxide or (1-6C)alkoxide, such as sodium or potassium methoxide or ethoxide. The sulfinic acid may itself be obtained by reacting 3,5-dimethylaniline with the appropriate phenylacetic acid of formula III (or a reactive derivative thereof such as the chloride, bromide or anhydride) under analogous conditions to those used in the acylation process (a) above, to give the corresponding N-acyl-3,5-dimethylaniline. The acylation is generally performed with an excess of the acylating agent in the presence of a base such as triethylamine in a suitable solvent or diluent such as t-butyl methyl ether or tetrahydrofuran and at a temperature of, for example, 10° to 40° C. and conveniently at or near ambient temperature. The N-acyl-3,5-dimethylaniline is then chlorosulfonated by reaction with chlorosulfonic acid to give the (4-N-acylamino-2,6-dimethylphenyl)sulfonyl chloride, which latter is reduced, for example, with a suitable sulfite (such as sodium sulfite) in the presence of a suitable buffer (such as sodium hydrogen carbonate) at a temperature of, for example, 60° to 90° C. to give the (4-N-acylamino-2,6-dimethylphenyl)sulfinic acid.

Alternatively, the sulfonyl chloride may also be obtained, for example, from the appropriate 4-N-acylamino-2,6-dimethylphenyl isothiocyanate by reaction with chlorine in water, using conditions analogous to those described by Johnson et alia in *J. Amer. Chem. Soc.*, 1939, 61, 2548. The isothiocyanate may itself be obtained, for example, by reaction of the appropriate 3,5-dimethyl-N-acylaniline with thiocyanogen (generated in situ from lead(II) thiocyanate and bromine in methyl acetate) or copper(II) thiocyanate in methyl or ethyl acetate.

Whereafter, when a pharmaceutically acceptable salt is required, a compound of formula I may be reacted with an appropriate base having a physiologically acceptable cation.

According to another aspect of the invention there is provided a pharmaceutical composition comprising a compound, of the formula I or a pharmaceutically acceptable salt thereof, together with a pharmaceutically acceptable diluent or carrier.

The compositions of the invention may be in various conventional forms. Thus, they may be in a form suitable for oral use (for example as tablets, lozenges, hard or soft capsules, aqueous or oily suspensions, emulsions, dispersible powders or granules, syrups or elixirs), for topical use (for example as creams, ointments, gels or aqueous or oily solutions or suspensions) or for parenteral administration (for example as a sterile aqueous or oily solution for intravenous, subcutaneous, intramuscular or intravascular dosing) or as a suppository for rectal dosing.

The compositions of the invention may be obtained by conventional procedures using conventional pharmaceutical excipients, well known in the art. Thus, compositions intended for oral use may contain, for example, one or more colouring, sweetening, flavouring and/or preservative agents and may be in the form of hard gelatin capsules in which the active ingredient is mixed with an inert solid diluent, for example, calcium carbonate, calcium phosphate or kaolin. Compositions for oral use may also be in the form of soft gelatin capsules in which the active ingredient is mixed with water or an oil such as arachis oil, liquid paraffin or olive oil.

Suitable pharmaceutically acceptable excipients for use in tablet formulations include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Aqueous suspensions will generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions will also typically contain one or more preservatives (such as ethyl or propyl R-hydroxybenzoate, anti-oxidants (such as ascorbic acid), colouring agents, flavouring agents, and/or sweetening agents (such as sucrose, saccharin or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, or esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art. Topical formulations for administration to the eye will generally be in the form of an ointment, gel or sterile solution buffered at an ophthalmically acceptable pH, for example in the range pH 7.0–7.6.

The amount of active ingredient that is combined with one or more excipients to produce a single dosage form will necessarily vary depending upon the host treated and the particular route of administration. For example, a formulation intended for oral administration to humans will generally contain for example from 0.5 mg to 1 g of active agent compounded with an appropriate and convenient amount of excipients which may vary from about 5 to about 98 percent by weight of the total composition. Dosage unit forms will generally contain about 1 mg to about 500 mg of an active ingredient.

As stated previously, the compounds of the invention inhibit the enzyme aldose reductase and are thus of value, for example, in treating those diseases or conditions which are caused by excessive quantities of the products such as sorbitol formed in the body by processes catalysed by the enzyme aldose reductase.

The property of inhibiting the enzyme aldose reductase in vivo may be demonstrated in the following standard laboratory test:

Rats are made diabetic (as evidenced by severe glucosuria being present) by dosing with streptozotocin. The animals are then dosed daily with the test compound for one, two or five days. The animals are then sacrificed 2–6 hours after the final dose and the eye lenses and/or sciatic nerves are removed. After a standard work-up procedure the residual sorbitol levels in each tissue are determined by gas liquid chromatography after conversion to the polytrimethylsilyl derivatives. Inhibition of aldose reductase in vivo can then be assessed by comparing the residual sorbitol levels in tissues from the dosed diabetic group of rats with those of an undosed group of diabetic rats and an undosed group of normal rats.

In a variation of the above test diabetic rats are dosed at a fixed daily oral dose for five days and then sacrificed 6 hours after the final dose and the reduction of sciatic nerve sorbitol assessed relative to that in control animals.

The property of inhibiting the enzyme aldose reductase may also be demonstrated in vitro. Thus, in a standard procedure partially purified aldose reductase is isolated in known manner from bovine lenses. The percentage inhibition of this enzyme's ability in vitro to catalyse the reduction of aldoses to polyhydric alcohols, and particularly to reduce glucose to sorbitol, caused by a test compound can then be determined using standard spectrophotometric methods.

In general, the majority of compounds of the invention show significant reduction of sciatic nerve sorbitol levels at a dose of 5 mg/kg or less in one of the above in vivo tests, together with an $IC_{50}$ in the above in vitro test in the order of $10^{-8}$M to $10^{-7}$M. As an illustration, the compound of Example 1 produced an 83% reduction in sciatic nerve sorbitol levels after 5 daily oral doses of 3 mg/kg and had an $IC_{50}$ of $11.8 \times 10^{-8}$M.

A compound of the formula I (or a pharmaceutically acceptable salt thereof) will primarily be administered systemically (generally by mouth) to a warm-blooded animal to produce a therapeutic or prophylactic effect mediated by inhibition of the enzyme aldose reductase, for example at a daily dose in the range of 1 to 40 mg/kg. In man, it is envisaged that a total daily dose in the range, for example, 15 to 800 mg. per man will be administered, given if necessary, in divided doses. However, the precise amount of the compound administered will naturally vary somewhat, for example, with the age and sex of the patient and the severity and extent of the condition being treated.

A compound of the formula I (or a pharmaceutically acceptable salt thereof) may also be administered topically, for example by direct topical administration to the tissue or organ in which inhibition of the enzyme is required, for example, to the eye. The precise amount of the compound administered will necessarily depend on the formulation used. Thus, for example, when a solution is administered, a concentration of the compound containing up to 0.01% by weight will generally be used. Similarly, when an ointment is administered a concentration of the compound of up to 2% by weight will generally be used. Topical formulations of a compound of the formula I (or a pharmaceutically acceptable salt thereof) may be administered to the eye of an animal, for example, man or dog, requiring treatment and/or prevention of diabetic cataracts or retinopathy, in a conventional manner, for example, using a drop or eyewash topical formulation.

A compound of the invention may be conveniently administered at or about the same time as one or more other agents which are known to have a useful effect in the treatment of diabetes or galactosemia, for example, a hypoglycaemic agent such as tolbutamide, chlorpropamide or glybenclamide. Any one or more such agents may also be conveniently present as an additional active ingredient in a composition according to the present invention.

Although the compounds of the invention are expected to be of use in the treatment or prophylaxis of human and animal diseases and conditions caused at least in part by elevated tissue sorbitol levels, they may be also be used whenever it is necessary to inhibit the enzyme known as aldose reductase either in vitro (for example during a research programme to discover other therapeutic agents) in vivo (for example in plants, when it is desired to modify their development by affecting the metabolism/utilisation of aldoses).

The invention will now be illustrated by the following non-limiting Examples in which, unless otherwise stated:

(i) solvents were removed by rotary evaporation in vacuo with a bath temperature of 40°–50° C.;

(ii) all operations were carried out at room temperature, that is in the range 18°–26° C.;

(iii) column and flash chromatography was carried out on silica (Merck Art. 7736) and medium pressure liquid chromatography (MPLC) on silica (Merck Art. 9385), both materials available from E Merck and Co., Darmstadt, West Germany;

(iv) all end-products were characterised by microanalysis and NMR spectoscopy;

(v) yields are given for illustration only and are not necessarily the maximum attainable by diligent process development.

EXAMPLE 1

Phenylacetyl chloride (1.16 g, 7.5 mM) was added to a stirred suspension of calcium carbonate (1.0 g, 10.0 mM) and (4-amino-2,6-dimethylphenylsulfonyl)nitromethane (1.22 g, 5.0 mM) in dry tetrahydrofuran (THF; 20 mL). The mixture was stirred for 16 hours during which time carbon dioxide was slowly released. Ethanol (1.0 mL) was then added and the mixture stirred for a further hour in order to decompose excess phenylacetyl chloride. Ethyl acetate (100 mL) was then added and the insoluble material removed by filtration. The filtrate was washed first with water (50 mL) containing 2M hydrochloric acid (2.0 mL) and then with saturated sodium chloride solution (2×40 mL) and then dried ($MgSO_4$). The solvent was evaporated and the residue recrystallised from ethyl acetate. The solid obtained was washed with ether and air dried to give (2,6-dimethyl-4-[phenylacetamido]phenylsulfonyl)nitromethane as white crystals, having m.p. 158°–159 ° C. and in 54% yield after recrystallisation from ethanol; microanalysis, found: C, 56.7; H, 5.0; N, 8.0%; $C_{17}H_{18}N_2O_5S$ requires: C, 56.4: H, 5.0; N, 7.7%.

The starting amino derivative may be obtained as follows:

(1) N-Acetyl-3,5-dimethylaniline (obtained as a solid, 138° C., by acetylation of 3,5-dimethylaniline) is reacted with an excess of chlorosulfonic acid at 60° C., using an analogous procedure to that described in Organic Syntheses, Coll. Vol. I, at page 85, to give 4-acetamido-2,6-dimethylbenzenesulfonyl chloride as a solid [thin layer chromatographic analysis (TLC): Rf ca. 0.27 (SiO$_2$: ethyl acetate/-hexane 1:1 v/v)] in about 90% yield, which is used without drying or characterisation.

(2) The above sulfonyl chloride (10.95 g, 50 mmol) is added in portions to a vigorously stirred solution of sodium bicarbonate (8.4 g, 100 mmol) and anhydrous sodium sulfite (12 g, 95 mmol) in water (50 mL) at 70°–80° C. The temperature is kept at 70°–80C. by intermittent heating. When the addition is complete, the mixture is heated and stirred at 70°–80° C. for a further hour. The mixture is then allowed to cool to room temperature during 4 hours and acidified with 2M hydrochloric acid. The precipitated solid is collected by filtration, washed with water, air dried and to give 4-acetamido-2,6-dimethylbenzenesulfinic acid, as a solid in about 80% yield; TLC: Rf ca. 0.02 (silica: ethyl acetate). This acid is converted to its sodium salt by addition to a solution of sodium methoxide (1 equivalent) in methanol and evaporation of the resultant solution. The sodium salt is used without purification or characterisation.

(3) Nitromethane (6.72 mL, 124 mM) is added to a stirred solution of sodium methoxide (3.01 g, 55.8 mM) in N,N-dimethylformamide (DMF; 250 mL), cooled to 0° C. in an ice-bath. When the addition is complete, stirring is continued for an additional 30 minutes at 0° C. 4-Acetamido-2,6-dimethylbenzenesulfinic acid sodium salt (11.59 g, 56 mmol) is then added, followed immediately by iodine (7.2 g, 28.3 mmol). The mixture is stirred for 16 hours and allowed to attain room temperature. A concentrated solution of aqueous sodium sulfite is then added to partially decolourise the reaction mixture, which latter was is then poured into water (about 1 liter) and acidified with 2M hydrochloric acid. The aqueous mixture is extracted with ethyl acetate. The combined extracts are washed with water, then with brine, and dried (MgSO$_4$). The solvent is removed by evaporation and the residue is purified by medium pressure liquid chromatography (MPLC) on silica, eluting with ethyl acetate-hexane (1:10 v/v, gradually increasing to 1:5 v/v) to give (4-acetamido-2,6-dimethylphenylsulfonyl)nitromethane as a solid, m.p. 179°–180° C. [purified by trituration with methanol] in 21% yield; NMR (d$_6$-DMSO 2.08(3H, s), 2.54(6H, s), 6.42(2H, s), 7.51(2H, s), 10.26(1H, s); microanalysis, found: C,46.2; H,5.0; N,9.7%; C$_{11}$H$_{14}$N$_2$O$_5$S requires: C,46.15; H,4.9; N,9.8%.

(4) (4-Acetamido-2,6-dimethylphenylsulfonyl)nitromethane (11.5 g, 40 mM) is added in one portion to a boiling mixture of concentrated hydrochloric acid (22 mL), water (110 mL) and ethanol (45 mL). The mixture is stirred at reflux until a clear solution is formed (about 20 minutes) and then for a further 10 mins. The hot reaction mixture is then poured into an excess of ice-cold saturated sodium bicarbonate solution. The aqueous mixture is extracted with ethyl acetate. The combined extracts are washed with brine, dried (MgSO$_4$) and the solvent removed by evaporation to give (4-amino-2,6-dimethylphenylsulfonyl)nitromethane, as a solid, m.p. 132°–133° C. [after recrystallisation from ethanol] in 73% yield; NMR(d$_6$-DMSO, 200 MHz): 2.39(6H, s), 6.19(4H, s), 6.35(2H,s); microanalysis, found: C,44.5; H,4.9; N,11.6%; C$_9$H$_{12}$N$_2$O$_4$S requires: C,44.3; H,4.9; N,11.5%.

EXAMPLES 2–59

Using a similar procedure to that described in Example 1, but using the appropriate acyl chloride, the following (4-N-acylamino-2,6-dimethylphenylsulfonyl)nitromethanes of the invention may be obtained:

| Example | N-acyl group | m.p. (°C.) | recryst. solvent(s) | yield (%) |
|---|---|---|---|---|
| 2 | (2,4,6-trimethylphenyl)acetyl | 203–204 | EtOH | 72 |
| 3 | (2-methylphenyl)acetyl | 188–190 | Et$_2$O | 89 |
| 4 | (2-fluorophenyl)acetyl | 183–184 | Et$_2$O | 84 |
| 5 | (2-chlorophenyl)acetyl | 188–190 | Et$_2$O | 80 |
| 6 | (2-methoxyphenyl)acetyl | 140–142 | EtOH | 28 |
| 7 | 1-(4-chlorophenyl)-1-cyclopropanecarbonyl | 150–151 | EtOH | 68 |
| 8 | 1-(phenyl)-1-cyclopropanecarbonyl | 127–128 | Et$_2$O/Hexane | 69 |
| 9 | (4-ethoxyphenyl)acetyl | 124–126 | Et$_2$O/Hexane | 78 |
| 10 | (R,SS)-2-(phenyl)propionyl | 175–176 | EtOH | 71 |
| 11 | (4-methoxyphenyl)acetyl | 182–183 | Et$_2$O | 99 |
| 12 | (R,SS)-benzocyclobutanecarbonyl | 193–194 | EtOH | 80 |
| 13 | (2-bromophenyl)acetyl | 188–190 | EtOH | 79 |
| 14 | (2-nitrophenyl)acetyl | 218–220 | Et$_2$O | 46 |
| 15 | 2-(4-chlorophenyl)-2-methyl-propionyl | 197–198 | Et$_2$O | 75 |
| 16 | (4-methoxy-3-methylphenyl)acetyl | 143–144 | EtOH/Hexane | 69 |
| 17 | (3-fluorophenyl)acetyl | 139–141 | Et$_2$O | 73 |
| 18 | (R,SS)-2-methoxy-2-(2-fluorophenyl)acetyl | 154–155 | toluene | 35 |
| 19 | (2-trifluoromethylphenyl)acetyl | 194–196 | Et$_2$O | 79 |
| 20 | (3,4-difluorophenyl)acetyl | 180–182 | Et$_2$O | 82 |
| 21 | (2,6-dichlorophenyl)acetyl | 210–212 | Et$_2$O | 75 |
| 22 | (4-trifluoromethylphenyl)acetyl | 182–183 | Et$_2$O | 38 |
| 23 | (4-chlorophenyl)acetyl | 190–191 | Et$_2$O | 96 |
| 24 | (3-methylphenyl)acetyl | 168–170 | Et$_2$O | 63 |
| 25 | (3-methoxyphenyl)acetyl | 140–142 | EtOH | 28 |
| 26 | 1-phenylcyclopentanecarbonyl | 119–120 | EtOH | 35 |
| 27 | 1-(4-methoxyphenyl)- | 178–179 | EtOH | 52 |

-continued

| Example | N-acyl group | m.p. (°C.) | recryst. solvent(s) | yield (%) |
|---|---|---|---|---|
| | cyclopropanecarbonyl | | | |
| 28 | (2-naphthyl)acetyl | 174–175 | Et₂O/Hexane | 53 |
| 29 | (R,SS)-1-(4-chlorphenyl)-cyclobutanecarbonyl | 147–148 | EtOH | 36 |
| 30 | (1-naphthyl)acetyl | 213–214 | EtOH/Et₂O | 56 |
| 31 | (2-methyl-6-nitrophenyl)acetyl | 205–207 | Et₂O | 75 |
| 32 | (4-fluorophenyl)acetyl | 161–162 | Et₂O/Hexane | 90 |
| 33 | (3,4-dichlorophenyl)acetyl | 199–200 | EtOH | 60 |
| 34 | F(2,4-dichlorophenyl)acetyl | 190–192 | EtOAc/Hexane | 69 |
| 35 | (R,SS)-2-(4-isobutylphenyl)-propionyl | 116–118 | Et₂O/Hexane | 23* |
| 36 | (R)-3,3,3-trifluoro-2-methoxy-2-phenylpropionyl | 106–108 | MeOH/H₂O | 60 |
| 37 | (R,SS)-3,3,3-trifluoro-2-methoxy-2-phenylpropionyl | 110–112 | MeOH/H₂O | 66 |
| 38 | (R,SS)-2-methoxy-2-(2-methylphenyl)acetyl | 176–177 | EtOAc | 87 |
| 39 | (S)-2-methoxy-2-phenylacetyl | 138–140 | EtOAc | 75 |
| 40 | (R,SS)-1,2,3,4-tetrahydro-1-naphthoyl | 120–122 | EtOAc | 62 |
| 41 | (R)-2-methoxy-2-phenylacetyl | 140–141 | EtOAc/Et₂O | 64 |
| 42 | (R,SS)-2-methoxy-2-phenylacetyl | 169–170 | EtOAc/Hexane | 73 |
| 43 | (R,SS)-2-(2-chlorophenyl)-2-methoxyacetyl | 171–172 | Toluene | 76 |
| 44 | (R,SS)-2-(2-chlorophenyl)-2-isopropoxyacetyl | 180–181 | MeOH | 10 |
| 45 | 3-indenylcarbonyl | 222–224 | MeOH | 4 |
| 46 | (R,SS)-1-indanylcarbonyl | 181–183 | EtOAc | 9 |
| 47 | (R,SS)-2-(3-fluoro-2-methyl-phenyl-2-methoxyacetyl | 174–176 | Et₂O | 61 |
| 48 | (R,SS)-2-(2,6-difluorophenyl)-2-methoxyacetyl | 165–167 | Et₂O | 27 |
| 49 | (2,6-difluorophenyl)acetyl | 195–197 | Et₂O | 67 |
| 50 | (1-isochromanyl)carbonyl | 162–163 | EtOAc/Hexane | 31 |
| 51 | (R,SS)-2-cyano-2-(phenyl)propionyl | 120–121 | Toluene | 25 |
| 52 | (R,SS)-2-methoxy-2-(2-methoxyphenyl)acetyl | 177–178 | Et₂O | 87 |
| 53 | (R,SS)-2-(2,3-difluorophenyl)-2-methoxyacetyl | 132–133 | Et₂O/Hexane | 60 |
| 54 | (S)-2-phenylpropionyl | 133–134 | Et₂O/Hexane | 62 |
| 55 | (R)-2-phenylpropionyl | 137–138 | Et₂O/Hexane | 53 |
| 56 | (R,SS)-2-(2-methylphenyl)-propionyl | 142–143 | Et₂O/Hexane | 76 |
| 57 | (R,SS)-2-phenylbutyryl | 140–141 | Et₂O/Hexane | 49 |
| 58 | (R,SS)-2-ethoxy-2-phenylacetyl | 135–136 | Et₂O | 50 |
| 59 | (R,SS)-2-ethoxy-2-(2-methyl-phenyl)acetyl | 172–173 | Et₂O | 69 |

Notes:
1. The following abbreviations are used for solvents: Et₂O = ether; EtOH = ethanol; EtOAc = ethyl acetate; MEOH = methanol; H₂O = water.
2. Where ether or ether/hexane is indicated as the solvent(s), this was used to solidify the initially isolated reaction product rather than recrystallisation.
3. * The reaction product was first purified by flash chromatography on silica using dichloromethane as eluant.

The starting acyl chlorides may be obtained using a conventional procedure from the corresponding acids, which are well known and in the majority of cases are commercially available. However, the acids for use in Examples 38, 43, 44, 47, 48, 52, 53, 58 and 59 were obtained by the general procedure described by Reeve et al. in *Synthesis*, 1971 at page 133, which involves reacting the appropriate benzaldehyde with bromoform, potassium hydroxide and an excess of methanol (except for Ex. 44, where 2-propanol is used and for Exs. 58 and 59, where ethanol is used) at about 0° to 5° C. The acid for use in Example 40 was obtained by the procedure described by Dauben et al. in *J. Amer. Chem. Soc.*, 1951, 1399. The acid for use in Example 46 was obtained by the procedure described in *Synthesis*, 1987, 845. The acid for use in Example 50 was obtained by the procedure described in *Arch. Pharm.*, 1966, 299, 931 and that for use in Example 51, by the procedure described in *Arch. Pharm.*, 1972, 305, 54.

The production of the acyl chlorides is illustrated by the following preparation of (R,S)-2-methoxy-2-(phenyl)acetyl chloride:

Oxalyl chloride (2.2 mL, 25 mM) was added to a stirred solution of (R,S)-2-methoxy-2-(phenyl)acetic acid (3.32 g, 20 mM) in dichloromethane (10 mL). Dry N,N-dimethylformamide (1 drop) was added to catalyse the reaction and the mixture was stirred for 16 hours. The solvent was removed by evaporation to leave (R,S)-2-methoxy-2-(phenyl)acetyl chloride as a pale yellow oil, which was used without further purification.

EXAMPLE 60

3-Chloroperbenzoic acid (55–60%; 1.0 g, 2.9 mM) was added in portions to a solution of (2,6-dimethyl-4-[2-(2-methylphenyl)acetamido]phenylthio)nitromethane (A) (0.5 g, 1.45 mmol) in chloroform (25 mL) at ambient temperature. The mixture was heated under reflux for 2 hours then allowed to cool. The precipitate of 3-chlorobenzoic acid was removed by filtration. The filtrate was washed with an aqueous solution of sodium metabisulfite (2×50 mL). The organic phase was dried (MgSO₄) and the solvent removed by evaporation. The cream solid obtained was purified by chromatography on silica eluting with ethyl acetate/hexane (0→20% v/v) to give (2,6-dimethyl-4-[2-(2-methylphenyl)acetamido]phenylsulfonyl)nitromethane, as a cream coloured solid, m.p. 188°-190° C. (m.p. 196°-199° C. after recrystallisation from ether) in 55% yield; NMR (200 MHz, d₆-DMSO): 2.29(s, 3H), 2.55(s, 6H), 3.31(s, 2H), 6.44(s, 2H), 7.1-7.5(m, 4H), 7.52(s, 2H), 10.5(s, 1H).

The starting phenylthio derivative (A) may be obtained as follows:

(i) Sodium borohydride (2.5 g, 66 mM) was added in portions to an ice-water cooled suspension of 2,6-dimethyl-4-[2-(2-methylphenyl)acetamido]phenyl thiocyanate (B) (5.0 g, 16 mM) in ethanol (100 mL) and dimethoxyethane (100 mL). After 2 hours, water (200 mL) was added to the clear yellow solution. The mixture was acidified to pH4 with 2M HCl and extracted with ethyl acetate. The combined extracts were washed with water, then with saturated sodium chloride solution, and dried (MgSO₄). The solvent was removed by evaporation to yield 2,6-dimethyl-4-[2-(2-methylphenyl)acetamido]benzenethiol as a cream coloured solid (4.89 g) which was used without characterisation.

(ii) The above thiol (4.89 g, 17.16 mM) was added to a stirred solution of sodium hydroxide (1.4 g), 35 mM) in water (50 mL) under oxygen. After 10 minutes, nitromethane (0.93 mL, 17.2 mmol) was added dropwise. The mixture was cooled using an ice-bath and after 10 minutes a solution of potassium ferricyanide (5.7 g, 17.3 mM) in water (30 mL) was added in portions. The mixture was stirred at ambient temperature for 1 hour. A further portion of nitromethane (0.31 mL, 5.7 mM) was added, followed after 10 minutes by a solution of potassium ferricyanide (1.9 g, 5.7 mM) in water (20 mL). After 30 minutes, the aqueous mixture was extracted with ethyl acetate. The combined extracts were washed with water (2×50 mL), dried (MgSO₄) and the solvent was evaporated. The solid obtained was triturated with ethyl acetate and the solid was discarded. The filtrate was evaporated to yield (2,6-dimethyl-4-[2-(2-methylphenyl)acetamido]phenylthio)nitromethane (A) as a pale brown solid in 62% yield: NMR (CDCl₃, 200 MHz): 2.28(s, 3H), 2.4(s, 6H), 3.65(s, 2H}, 5.6(s, 2H), 7.1-7.22(m, 4H), 7.42(s, 2H), 10.14(s, 1H).

The starting thiocyanate (B) may be obtained as follows:

(iii) Cupric thiocyanate (28 g, 155.6 mM) was added to a stirred solution of 3,5-dimethylaniline (7.6 mL, 62.2 mM) in ethyl acetate (150 mL). The mixture was then heated at 60° C. for 2.5 hours, cooled to ambient temperature and solid material removed by filtration through a bed of diatomaceous earth.. The residue was washed well with ethyl acetate. The purple filtrate was then washed with 5% w/v (?) aqueous sodium bicarbonate. The pale yellow organic layer was separated, washed successively with water and saturated sodium chloride solution and dried (MgSO₄). The solvent was removed evaporation and the solid obtained was triturated with ether to give 4-amino-2,6-dimethylphenyl thiocyanate, as a cream coloured solid 65% yield: NMR: 2.37(s, 6H), 6.43(s, 2H).

(iv) 2-(2-Methylphenyl)acetyl chloride (9.9 g, 58.8 mM) was added to a stirred suspension of calcium carbonate (7.87 g, 78.7 mM) and 4-amino-2,6-dimethylphenyl thiocyanate (7 g, 39.3 mM) in dry THF (150 mL). The mixture was stirred for 1 hour. Water (1000 mL) was added. The mixture was acidified to pH4 with 2M HCl and extracted with ethyl acetate. The combined extracts were washed with water, then with saturated sodium chloride solution and dried (MgSO₄). The solvent was removed by evaporation. The pale green solid obtained was triturated with ether to give 2,6-dimethyl-4-[2-(2-methylphenyl)acetamido]phenyl thiocyanate (B), as a cream coloured solid in 83% yield; NMR (CDCl₃, 200 MHz): 2.47(s, 3H), 2.49(s, 6H), 3.69(s, 2H), 7.14-7.17(m, 4H), 7.55(s, 2H), 10.27(s, 1H).

Alternatively steps (i) and (ii) may be telescoped for the production of the phenylthio derivative (A) as follows:

Sodium borohydride (0.24 g, 6.3 mM) was added in portions to a stirred suspension of 2,6-dimethyl-4-[2-(2-methylphenyl)acetamido]phenyl thiocyanate (0.5 g, 1.6 mM), in ethanol (20 mL). After 30 minutes, acetone (0.47 mL, 6.4 mM) was added to remove excess sodium borohydride and the mixture stirred for 10 minutes to give a clear yellow solution containing 2,6-dimethyl-4-[2-(2-methylphenyl)acetamido]benzenethiol. Nitromethane (0.09 mL, 1.6 mM) was then added followed, after 10 minutes, by a solution of potassium ferricyanide (0.53 g, 1.6 mM) in water (10 mL). Progress of the reaction was followed by standard thin layer chromatographic (tlc) analysis. After 1 hour, unreacted thiol remained and so further nitromethane (0.45 mL, 0.8 mM) and a solution of potassium ferricyanide (0.27 g, 0.8 mM) in water (5 mL) was added. After about a further 1 hour, thiol was no longer detectable by tlc analysis. Water (500 mL) was then added. The reaction mixture was acidified to pH4 with 2M HCl and extracted with ethyl acetate. The extracts were dried (MgSO₄) and the solvent evaporated. The sticky, orange solid was triturated with ether. The orange filtrate was separated and the solid residue discarded. The filtrate was evaporated to give (2,6-dimethyl-4-[2-(2-methylphenylacetamido]phenylthio)nitromethane as an orange/brown solid, m.p. 152° C. (decomposition) in 20% yield and which was used without purification.

EXAMPLE 61

Nitromethane (5.4 mL, 98 mM) was added to a stirred solution of sodium methoxide (2.7 g, 49 mM) in N,N-dimethylformamide (DMF; 250 mL), cooled to about 0° C. When the addition was complete, stirring was continued for an additional 30 minutes at about 0° C. 4-(4-[2-Trifluoromethylphenyl]acetamido)-2,6-dimethylbenzenesulfinic acid sodium salt (16.9 g, 43 mM) (estimated by NMR analysis to be no more than 50% strength) was then added, followed immediately by iodine (6.35 g, 49 mM). The mixture was stirred for 16 hours and allowed to attain room temperature. A concentrated solution of aqueous sodium sulfite was then added to partially decolourise the reaction mixture, which latter was then poured into water (about 1L). The aqueous mixture was acidified with 2M hydrochloric acid and extracted with ethyl acetate. The combined extracts were washed with water, then with saturated sodium chloride solution, and dried (MgSO₄). The solvent was removed by evaporation and the residue was purified by vacuum flash chromatography on 60H silica, eluting with ethyl acetate-hexane (1:10 v/v, gradually increasing to 1:5 v/v) to give (4-[2-(2-trifluoromethylphenyl)acetamido]-2,6-dimethylphenylsulfonyl)nitromethane as a solid, m.p. 203°–204° C. (after crystallisation from ethyl acetate/hexane) in 10% yield; NMR (d₆-DMSO, 200 MHz): 2.55(6H, s), 3.8(2H, s), 6.45(2H, s), 7.55(4H, m,), 7.7(2H, d), 10.56(1H, s); microanalysis, found: C, 50.3; H, 4.0; N, 6.4%; $C_{18}H_{17}N_2O_5S\ F_3$ requires: C, 50.2; H, 3.98; N, 6.51%.

The starting sulfinic acid may be obtained as follows:
(i) 4-(2-[2-Trifluoromethylphenyl]acetyl)-3,5-dimethylaniline (obtained as a solid, m.p. 168° C., by reacting 2-(2-trifluoromethylphenyl)acetyl chloride with 3,5-dimethylaniline in THF solution in the presence of calcium carbonate) was reacted with an excess of chlorosulfonic acid at 60° C. using an analogous procedure to that described in *Organic Synthesis*, Coll. Vol. I, at page 85, to give 4-(2-[2-trifluoromethylphenyl]acetamido)-2,6-dimethylbenzenesulfonyl chloride, as a solid in about 47% yield, which was used without purification.

(ii) The above sulfonyl choloride (17.4 g, 43 mM) was added in portions to a vigorously stirred solution of sodium bicarbonate (7.9 g, 46 mM) and anhydrous sodium sulfite (11.5 g, 92 mM) in water (92 mL) at 70°–80° C. The temperature was kept at 70°–80° C. by intermittent heating. When the addition was complete, the mixture was heated and stirred at 70–80° C. for a further hour. The mixture was then allowed to cool to room temperature during 4 hours and acidified with 2M hydrochloric acid. The precipitated solid was collected by filtration, washed with water, air dried to give crude 4-(2-[2-trifluoromethylphenyl]acetamido)-2,6-dimethyl-benzenesulfinic acid, as a low melting point solid contaminated with sodium sulfate and the corresponding sulfonic acid. This acid was converted to its sodium salt by addition of a solution of sodium methoxide in methanol to pH9 and evaporation of the resultant solution. The sodium salt was used without purification or characterisation.

EXAMPLES 62–74

Using a similar procedure to that described in Example 1 but starting from the appropriate acyl chloride in place of phenylacetyl chloride the following (4-N-acylamino-2,6-dimethylphenylsulfonyl)nitromethanes of the invention may be obtained:

| Example | N-acyl group | m.p. (°C.) | recryst. solvent(s) | yield (%) |
|---|---|---|---|---|
| 62 | (+)-2-methoxy-2-(2-methylphenyl)acetyl | 152–153 | EtOAc note (a) | 84 |
| 63 | (R,SS)-2-ethoxy-2-(2-fluorophenyl)acetyl | 132–133 | Et₂O | 61 |
| 64 | 2-(2,3-dimethylphenyl)acetyl | 210–211 | Et₂O | 27 |
| 65 | 2-(2,6-dimethylphenyl)acetyl | 213–215 | Et₂O | 45 |
| 66 | (R,SS)-2-(2,6-difluorophenyl)-propionyl | 82–84 | EtOAc/Hexane | 20 |
| 67 | (−)-2-methoxy-2-(2-methylphenyl)acetyl | 163–164 | EtOAc Note (b) | 79 |
| 68 | 2-(4-methylphenyl)acetyl | 163–164 | Et₂O | 85 |
| 69 | 2-(2-fluorophenyl)propionyl | 111–113 | EtOAc/Hexane | 15 |
| 70 | 2-(2,4-dimethylphenyl)acetyl | 173–174 | EtOAc/Hexane | 78 |
| 71 | (−)-1,2,3,4-tetrahydro-1-naphthoyl | 180–181 | EtOAc (note (c)) | 60 |
| 72 | (+)-1,2,3,4-tetrahydro-1-naphthoyl | 178–180 | EtOAc Note (d) | 50 |
| 73 | (−)-2-methoxy-2-(2-methoxyphenyl)acetyl | 138–139 | Et₂O Note (e) | 87 |
| 74 | (+)-2-methoxy-2-(2-methoxyphenyl)acetyl | 139–141 | Et₂O Note (f) | 86 |

(1) The following optical rotations were obtained for individual enantiomers obtained above at the sodium D line at approximately 20° C. (c = 1, in ethanol or ethyl acetate as solvent):-

| Note | [α]_D | Solvent |
|---|---|---|
| (a) | +71° | EtOAc |
| (b) | −69°. | EtOAc |
| (c) | −42° | EtOAc |
| (d) | +40° | EtOAc |
| (e) | −80° | EtOAc |
| (f) | +77° | EtOAc |

(2) The starting acyl chlorides may be obtained from the corresponding carboxylic acids by conventional procedures such as that described above for (R,SS)-2-methoxy-2-(phenyl)acetyl chloride. The starting carboxylic acids are in general already known or may be obtained by conventional procedures well known in the art. For example, 2-ethoxy-2-(2-fluorophenyl)acetic acid may be obtained as follows:-
A solution of potassium hydroxide (22.4 g, 42.8 mill) in ethanol (88 mL) was added during 3 hours to a stirred mixture of -continued

| Example | N-acyl group | m.p. (°C.) | recryst. solvent(s) | yield (%) |
|---------|--------------|------------|---------------------|-----------|

2-fluorobenzaldehyde (10.0 g, 80.5 mM) and bromoform (24.3 g, 6.0 mM) in ethanol (40 mL) at 0° C. The mixture was then allowed to warm to ambient temperature and stirred overnight. Water (100 mL) and 50% v/v saturated sodium chloride solution (30 mL) were then added. The mixture was extracted with ether and the extracts discarded. The aqueous phase was warmed to remove traces of ether, acidified to pH3 with 2 M hydrochloric acid, and then extracted with ethyl acetate (2 × 100 mL). The extracts were combined, washed with saturated sodium chloride solution, dried ($MgSO_4$) and the solvent evaporated to leave 2-ethoxy-2-(2-fluorophenyl)acetic acid as a pale brown oil which was used without further purification in the production of the corresponding acid chloride.

(3) The separate enantiomers of (R,SS)-2-methoxy-2-(2-methoxyphenyl)acetic acid may be obtained by the following resolution procedure:-
(R,SS)-2-methoxy-2-(2-methoxyphenyl)acetic acid (20.75 g, 105.9 mM) was dissolved in hot ethanol (53 mL) and added quickly to a vigorously stirred, hot solution of (1S,2R)-(+)-ephedrine (17.5 g, 105.9 mM) in ethanol (50 mL). The mixture was allowed to cool to ambient temperature. The white solid obtained was collected by filtration and recrystallised from ethanol to give a crystalline ephedrine salt (15.65 g). This salt was dissolved in water (150 mL). The solution was acidified by adding 1 equivalent of M hydrochloric acid (43 mL) and then extracted with ethyl acetate (2 × 100 mL). The extracts were washed with water, then with saturated sodium chloride solution, dried ($MgSO_4$) and the solvent evaporated to give (+)-2-methoxy-2-(2-methoxyphenyl)acetic acid as an oil, which slowly crystallised to give solid (8.0 g), $<[\alpha]_D = +151.8°$ ($c = 1$, EtOH); optical purity 97.6% e.e. [by NMR analysis using the NMR shift reagent (R)-(−)-TFAE].
Using an analogous procedure but adding (1R,2S)-(−)-ephedrine to (R,SS)-2-methoxy-2-(2-methoxyphenyl)acetic acid there was obtained (−)-2-methoxy-2-(2-methoxyphenyl)acetic acid as a white crystalline solid (overall yield 36.5%), $^{21}[\alpha]_D = -158.9°$ (sd,8 $c = 1$, EtOH); optical purity 99.5% e.e.[by NMR analysis using (R)-(−)-TFAE].

(4) The separate (R) and (S) enantiomers of (R,SS)-1,2,3,4-tetrahydro-1-naphthoic acid may be obtained using essentially the same procedure to that described by Westman in Arkiv für Kemi, 1958, 12(17), 161.

(5) The separate (R) and (S) enantiomers of (R,SS)-2-methoxy-2-(2-methylphenyl)acetic acid may be obtained by analogous resolution procedures to that described in note (3) hereinabove and had the following properties:
(+)-form: m.p. 69-70° C.; $^{22}[\alpha]_D = +145°$ (sd,8 $c = 1$, ethyl acetate); optical purity 99.5% e.e. [by NMR analysis using (R)-(−)-TFAE];
(−)-form: m.p. 66-68° C.; $^{22}[\alpha]_D = -139°$ (sd,8 $c = 1$, ethyl acetate); optical purity 98.3% e.e. [by NMR analysis using (R)-(−)-TFAE];

EXAMPLE 75

A solution of (2,6-dimethyl-4-[2-methoxy-2-(2-methoxyphenyl)acetamido]phenylsulfonyl)nitromethane (2 mM) in methanol (50 mL) was treated with a solution of sodium methoxide (2.05 mM) in methanol (30 mL) cooled to about 5° C. The mixture was stirred for 10 minutes and then the solvent removed by evaporation to give (2,6-dimethyl-4-[2-methoxy-2-(2-methoxyphenyl)acetamido]phenylsulfonyl)nitromethane sodium salt as a deliquescent solid residue, in essentially quantitative yield.

EXAMPLE 76

The following illustrate representative pharmaceutical dosage forms containing a compound of the formula I, such as is described in any one of the previous Examples (or a pharmaceutically acceptable salt thereof), for therapeutic or prophylactic use in humans:

|  | mg/tablet |
|---|---|
| (a) Tablet I | |
| Compound | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |
| Compound | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | |
| Compound | 10 |
| Lactose Ph.Eur | 488.5 |

-continued

| | mg/tablet |
|---|---|
| Magnesium stearate | 1.5 |

The above formulations may be obtained by conventional procedures well known in the pharmaceutical art. If required, the tablets (a)–(c) may conveniently be enteric coated by conventional means, for example to provide a coating of cellulose acetate phthalate.

CHEMICAL FORMULAE

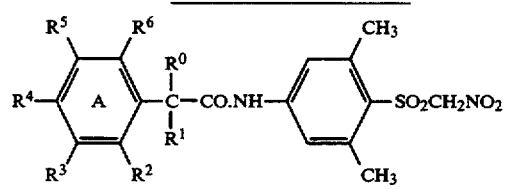

I

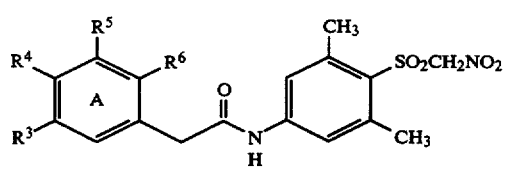

Ia

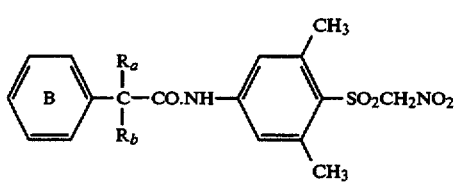

II

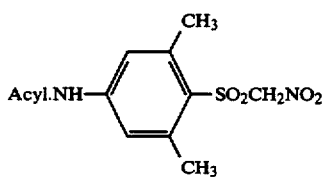

Q

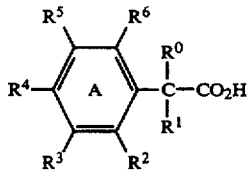

III

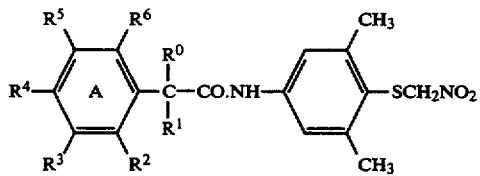

IV

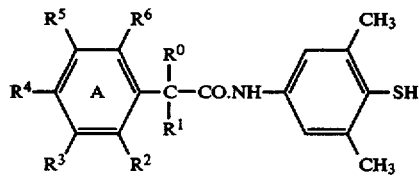

V

-continued
CHEMICAL FORMULAE

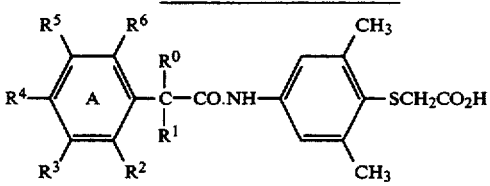

VI

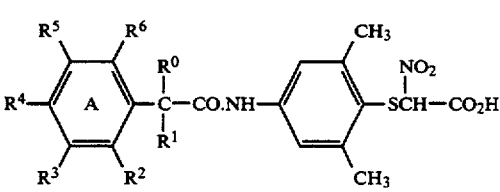

VII

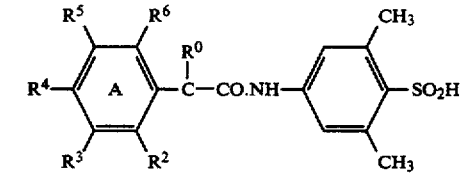

VIII

What is claimed is:

1. A phenylacetyl derivative of the compound (4-amino-2,6-dimethylphenylsulphonyl)nitromethane having the formula I:

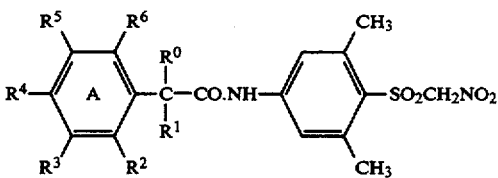

I wherein $R^0$ and $R^1$ are independently hydrogen, (1–4C)alkyl, (1–4C)alkoxy, or trifluoromethyl, or together constitute (2–6)alkylene, or $R^1$ together with $R^2$ of the adjacent benzene ring A constitutes methylene, ethylene, vinylene, trimethylene or tetramethylene; and an adjacent pair of the available $R^2$, $R^3$, $R^4$, $R^5$ and $R^6$ completes (together with the adjoining carbon atoms) a further benzene ring which may itself optionally bear a halogeno, (1–4C)alkyl or (1–4C)alkoxy substituent, another of $R^2$–$R^6$ is hydrogen, halogeno, trifluoromethyl, nitro, (1–4C)alkyl or (1–4C)alkoxy, and the remainder of $R^2$–$R^6$ is hydrogen; or when $R^0$ and $R^1$ together constitute (2–6C)alkylene or when $R^1$ together with $R^2$ of the adjacent benzene ring A constitutes methylene, ethylene, vinylene, trimethylene or tetramethylene on benzene ring A, one two or three of the available $R^2$, $R^3$, $R^4$, $R^5$ and $R^6$ are additionally independently selected from hydrogen, halogeno, trifluoromethyl, nitro, (1–4C)alkyl and (1–4C)alkoxy, and the remainder of $R^2$–$R^6$ is hydrogen; or a pharmaceutically acceptable salt thereof.

2. A compound as claimed in claim 1 wherein $R^0$ and $R^1$ are selected from hydrogen, methoxy, ethoxy, isopropoxy or trifluoromethyl, or $R^0$ and $R^1$ together constitute ethylene, 1,1-dimethylethylene, trimethylene, tetramethylene or pentanethylene, or $R^1$ together with $R^2$ of the adjacent benzene ring A constitutes methylene, ethylene, vinylene, trimethylene or tetramethylene; and an adjacent pair of the available $R^2$, $R^3$, $R^4$, $R^5$ and $R^6$ completes (together with the adjoining carbon atoms) a further benzene ring which may itself optionally bear a fluoro, chloro, methyl or methoxy substituent, another of $R^2$–$R^6$ is hydrogen, fluoro, chloro, bromo, trifluoromethyl, nitro, methyl, ethyl, propyl, isopropyl, isobutyl, methoxy and ethoxy, and the remainder of $R^2$–$R^6$ is hydrogen; or when $R^0$ and $R^1$ together constitute ethylene, 1,1-dimethylethylene, trimethylene, tetramethylene or pentamethylene, or when $R^1$ together with $R^2$ of the adjacent benzene ring A constitutes methylene, ethylene, vinylene, trimethylene or tetramethylene on benzene ring A, one, two or three of the available $R^2$, $R^3$, $R^4$, $R^5$ and $R^6$ are additionally independently selected from hydrogen, fluoro, chloro, bromo, trifluoromethyl, nitro, methyl, ethyl, propyl, isopropyl, isobutyl, methoxy and ethoxy, and the remainder of $R^2$–$R^6$ is hydrogen.

3. A compound as claimed in claim 1 or 2 wherein $R^0$ and $R^1$ have one of the following combinations (a)–(e):
(a) $R^0$ and $R^1$ are both hydrogen; (b) $R^0$ is hydrogen and $R^1$ is methyl; (c) $R^0$ is hydrogen and $R^1$ is ethyl; (d) $R^0$ is hydrogen or trifluoromethyl, and $R^1$ is methoxy or ethoxy; or (e) $R^0$ and $R^1$ together constitute ethylene.

4. A bi- or tri-cyclic amide of the formula Ia:

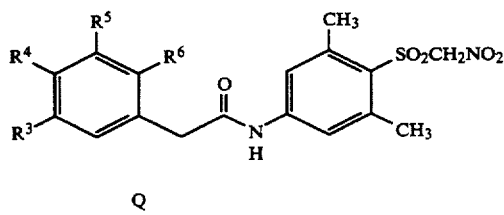

wherein Q is methylene, ethylene, vinylene or trimethylene and the substituents $R^3$–$R^6$ on benzene ring A have any of the meanings defined in claim 1 or 2, or a pharmaceutically acceptable salt thereof.

5. A pharmaceutically acceptable salt as claimed in claim 1, which is selected from alkali metal, alkaline earth metal, ammonium and aluminium salts, and from salts with an organic base affording a physiologically acceptable cation.

6. A pharmaceutical composition which comprises a pharmaceutically effective amount of a compound of formula I, or a pharmaceutically acceptable salt thereof, as defined in claim 1, together with a pharmaceutically acceptable diluent or carrier.

7. A method of inhibiting the enzyme aldose reductase in a warm-blooded animal requiring such treatment which comprises administering to said animal an effective amount of a compound of the formula I, or a pharmaceutically acceptable salt thereof, as defined in claim 1.

8. A method of treating or preventing one or more of the peripheral side-effects of diabetes or galactosemia caused at least in part by the accumulation of sorbitol or galactitol in a warm blooded animal requiring such treatment which comprises administering to said animal an effective amount of a compound of the formula I, or a pharmaceutically acceptable salt thereof, as defined in claim 1.

9. A compound of the formula IIa:

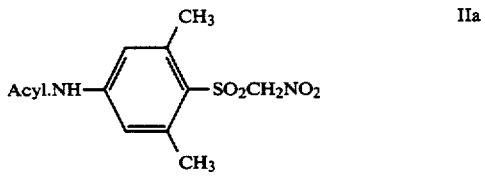

wherein Acyl is selected from:
1-(4-chlorophenyl)-1-cyclopropanecarbonyl,
1-(phenyl)-1-cyclopropanecarbonyl,
(R,S)-benzocyclobutanecarbonyl,
1-phenylcyclopentanecarbonyl,
1-(4-methoxyphenyl)-cyclopropanecarbonyl,
(2-naphthyl)acetyl,
(R,S)-1-(4-chlorophenyl)-cyclobutanecarbonyl,
(1-naphthyl)acetyl,
(R,S)-1,2,3,4-tetrahydro-1-naphthoyl, 3-indenylcarbonyl,
(R,S)-1-indanylcarbonyl,
(R)-1,2,3,4-tetrahydro-1-naphthoyl, and
(S)-1,2,3,4-tetrahydro-1-naphthoyl; or
a pharmaceutically acceptable salt thereof.

10. A compound of the formula

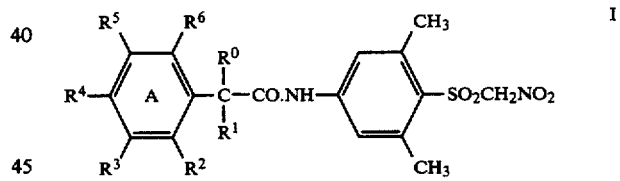

selected from:
(R,S)-(2,6-dimethyl-4-[1,2,3,4-tetrahydro-1naphthoylamino]phenyl-sulphonyl)nitromethane, and
(−)-(2,6-dimethyl-4-[1,2,3,4-tetrahydro-1-naphthoylamino]phenylsulphonyl)nitromethane; or
a pharmaceutically acceptable salt thereof.

* * * * *